on Patent [19]

Motosugi et al.

[11] Patent Number: 4,699,135
[45] Date of Patent: Oct. 13, 1987

[54] SHAPED CHITIN BODY

[75] Inventors: Kenzo Motosugi, Kyoto; Koji Kifune, Nara; Yasuhiko Yamaguchi, Kyoto; Yasuo Nobe, Kyoto; Hiroyuki Tanae, Kyoto, all of Japan

[73] Assignee: Unitika Ltd., Amagasaki, Japan

[21] Appl. No.: 761,260

[22] Filed: Aug. 1, 1985

[30] Foreign Application Priority Data

Aug. 3, 1984 [JP] Japan .................................. 59-164016
Aug. 21, 1984 [JP] Japan .................................. 59-173944

[51] Int. Cl.$^4$ ............................................ A61F 15/00
[52] U.S. Cl. ........................................ 128/156; 530/356
[58] Field of Search ........................ 128/156; 530/356

[56] References Cited
U.S. PATENT DOCUMENTS
4,655,980 4/1987 Chu ...................................... 128/156

Primary Examiner—Gregory E. McNeill
Attorney, Agent, or Firm—Sughrue, Mion, Zinn, Macpeak and Seas

[57] ABSTRACT

A shaped chitin body prepared by treating a shaped body of chitin with an alkali solution, such that within a dilute aqueous solution of acetic acid, the volume of said shaped chitin body will increase by a factor of at least about 10 while substantially retaining its shape. This shaped chitin body has versatile capabilities comparable to those of chitosan. A nonwoven fabric made of a fibrous chitin body is particularly effective as a wound dressing.

17 Claims, No Drawings

SHAPED CHITIN BODY

FIELD OF THE INVENTION

The present invention relates to a novel shaped chitin body having both the strength properties of chitin and the versatile capabilities of chitosan. The present invention also relates to a wound dressing made of chitin fibers having such properties.

BACKGROUND OF THE INVENTION

In spite of its abundant supply in nature, chitin has not been utilized to the fullest extent and its effective utilization is strongly desired. Many proposals have been made for possible applications of chitin and chitosan; see, for example, *Kagaku to Seibutsu* (*Chemistry and Biology*), Vol. 21, p. 635 (1983). However, very few cases of successful commercialization of chitin and chitosan have been reported, primarily because of the non-existence of established technology for shaping these polysaccharides. For example, in order to exploit the metal adsorbing and ion exchange capabilities of chitosan on an industrial scale, efficient techniques for shaping and processing chitosan are necessary, but no such techniques have yet been established in the art.

The following comparisons can be made between shaped bodies of chitin and chitosan. First, chitin is stronger than chitosan, whereas the latter has more versatile capabilities, for example, ion exchange, metal adsorption, and antifungal properties. The solubility of chitosan in aqueous acid solutions proves advantageous for the purpose of shaping and processing chitosan, but has turned out to be a serious problem hindering commercial application of shaped chitosan bodies. It has therefore been strongly desired to develop a practical shaped body that has capabilities comparable to those of chitosan and yet does not dissolve in acid.

One of the greatest concerns in the fields of plastic surgery and dermatology is the development of effective methods for healing skin defect wounds such as burns and lesions left after skin excision. Wound dressings are indispensable for this purpose and a lot of materials have been investigated. Synthetic wound dressings so far proposed include specially woven fabrics of nylon, polyester, polypropylene or rayon (wherein monofilaments with a diameter of several hundred microns form surface projections in the form of loop piles or nappings), laminations of these fabrics and a silicone sheet, sponges of formylated polyvinyl alcohol, gels of a block copolymer of ethylene oxide and polyoxypropylene glycol, and "Sofratulle" (a gauze available from Nippon Roussel, impregnated with an antibiotic containing ointment). Wound dressings made of biological materials include nonwoven fabrics made of fibrin membrane, plasma membrane, and even collagen fibers (such nonwoven fabrics are sold, e.g., by Meiji Seika, Ltd. under the trademark "MEIPAC"), as well as porcine skins prepared by sterile freeze-drying of the dermis of the back of pigs. Several of the wound dressings mentioned above are described in *Geka-Shinrvoshi* (*Journal of Surgical Diaqnosis*), February 1975, p. 121.

However, none of the wound dressings proposed so far are completely satisfactory as protective materials for skin defect wounds. The general functions of wound dressings are the prevention of any loss of body tissues from the wound surface, prevention of infection, and assisting in the formation of granulation and epidermis. In order to retain these functions until a regenerating skin forms, ideal wound dressings must satisfy various requirements such as high strength, good adhesion to the lesion, high water abscrption, high adsorbability of exudates, high moisture permeability, histocompatibility, the absence of antigenicity, and the ability to promote skin regeneration. Nevertheless, the existing wound dressings made of synthetic materials are low in water absorption, adsorbability of exudates, and moisture permeability, whereas wound dressings made of naturally occurring substances are particularly low in strength and adsorbability of exudates, and are readily liquefied so as to become pulpy in only a few days after being applied to deep wounds. As a result, the conventional synthetic or natural wound dressings used to protect wounds have been unable to realize fully satisfactory formation of the granulation or epidermis. Burns are divided into the following four degrees in increasing order of severity: first degree, superficial second degree, deep second degree, and third degree burns. Existing wound dressings have been applied to the therapy of first degree burns and superficial second degree burns exclusively. In a similar manner, lesions that are left after excising split thickness grafts are the only wounds that can be treated at all by the conventional wound dressings.

SUMMARY OF THE INVENTION

As a result of various studies made to develop a shaped chitin body that will exhibit a satisfactory performance from a practical viewpoint, the present inventors have found that a shaped chitin body can be provided with both acid resistance and capabilities comparable to those of chitcsan by means of alkali treatment. The inventors have also found that a wound dressing made of alkali treated chitin fibers has good adhesion to the lesion and permits effective adsorption of exudates without causing their stagnation. The dressing will not be liquefied or damaged until after the wound heals completely, as indicated by the formation of the intended granulation and epidermis. The present invention has been accomplished on the basis of these findings.

The shaped chitin body in accordance with the present invention is prepared by treating a shaped body of chitin with an alkali solution, such that within an aqueous solution of dilute acetic acid, the volume of the shaped chitin body will increase by a factor of at least about 10 while retaining its shape. This shaped body has both the versatile capabilities of chitosan and the strength properties of chitin. If the alkali treated chitin is in the fibrous form, it will swell in a 2 v/v% (i.e., % on a volume/volume basis) aqueous solution of acetic acid at 25° C. so that its cross sectional area expands to at least 10 times its initial value. Nonwoven fabrics or fibrous sheets composed of such chitin fibers have properties proving most effective for use as wound dressings.

DETAILED DESCRIPTION OF THE INVENTION

The term "chitin" as used herein covers both poly(N-acetyl-D-glucosamine) per se and derivatives thereof. Chitin as included within this definition may be prepared by treating the exoskeletons of crustaceans and insects with hydrochloric acid and caustic soda to remove calcium carbonate and proteins. The purified product may be further treated to produce derivatives by, for example, etherization or esterification. Chitin derivatives that are preferably used in the present invention include etherized chitins such as carboxymethylated chitin and hydroxyethylated chitin, and esterified chitins such as acetylated chitin and sulfonated chitin. Illustrative acid components of the appropriate esters include carboxylic acids such as formic acid, acetic acid, butyric acid, valeric acid, isobutyric acid, isovaleric acid, benzoic acid, cinnamic acid, salicylic acid, anthranilic acid and phthalic acid; sulfuric acid; sulfonic acids such as toluenesulfonic acid and sulfanilic acid; carbonic acids; and esters of these acids.

The shaped chitin body of the present invention is prepared by treating a shaped body of chitin with an alkali. The shaped body of chitin to be subjected to the alkali treatment is prepared by first dissolving chitin or a derivative thereof in a suitable solvent, then imparting a shape to the solution, and coagulating the same. Examples of suitable solvents include mixtures of trichloroacetic acid and hydrocarbon halides such as methylene chloride, N-methylpyrrolidone containing lithium chloride, and dimethylacetamide containing lithium chloride. For ensuring good chitin dissolvability, the concentration of lithium chloride is preferably at least 5 w/w % (i.e., % on a weight/weight basis). The concentration of chitin in solution will vary with the degree of its polymerization and is preferably in the range of 0.05 to 50 w/w %, with the range of 0.1 to 25 w/w % being more preferred. An optimum chitin concentration is in the range of from 0.3 to 10 w/w %.

The shaped body of chitin to be subjected to alkali treatment may be in any form that is adapted to the specific use intended for the final chitin shaped body to be produced in accordance with the present invention, and illustrative forms that may be assumed by the shaped body of chitin are particulate and fibrous.

The particulate chitin in accordance with the present invention comprises particles having a substantially uniform shape and size, and exemplary shapes of the particles include spherical, rice grain-like, cylindrical, disk-like and other special shapes. The individual particles preferably range from 0.001 to 10 mm in terms of length, major axis or diameter. The fibrous chitin in accordance with the present invention includes both a multifilament composed of monofilaments with a diameter preferably in the range of from 0.001 to 0.1 mm and/or monofilament with a preferred diameter of 0.05 to 10 mm. They may assume any cross-sectional shape, and include hollow fibers.

The alkali treatment to which the above described shaped body of chitin is subjected includes any method that permits the preshaped chitin to come into contact with an alkali solution. A practical alkali solution is an aqueous solution of sodium hydroxide having a concentration which is preferably at least 0.1 w/v % (i.e., % based on the weight of sodium hydroxide (g)/volume of alkali solution (cc)), more preferably at least 10 w/v %, and optimally in the range of from 30 to 60 w/v %. The preferred temperature for alkali treatment is at least 10° C., more preferably at least 40° C., and optimally ranges from 60° to 120° C. The duration of alkali treatment will vary depending upon the alkali concentration and treatment temperature, and the preferred duration generally being in the range of from 1 minute to 24 hours, with the range of from 15 minutes to 12 hours being more preferred. An optimum range is from 1 to 6 hours.

If a 40 w/v % aqueous solution of sodium hydroxide is used as the alkali agent, exemplary preferred treatment conditions include 70° C. ×5 hours, 80° C.×3 hours, or 120° C.×1 hour.

The preferred bath ratio for use in the alkali treatment is such that at least 25 parts by weight of the alkali solution is used for one part by weight of the shaped body of chitin. More preferably, at least 50 parts, and most preferably, at least 100 parts, by weight of the alkali solution may be used per part by weight of the shaped body of chitin. The alkali solution may be stirred, if desired, to assure better contact. If alkali removal is desired after the treatment, neutralization and washing with water may be followed by treatment with an organic solvent and drying. Useful drying methods include natural drying, forced air drying, vacuum drying, spray drying, and freeze drying.

The shaped chitin body prepared by treating a shaped body of chitin in accordance with the present invention has such a nature that it swells in a dilute aqueous solution of acetic acid to have its volume increased by a factor of at least about 10, sometimes as much as about 1,000, while substantially retaining its initial shape. The terminology "dilute aqueous solution of acetic acid" as used herein means aqueous solutions containing from 0.1 to 50 v/v % of glacial acetic acid. The preferred concentration of glacial acetic acid ranges from 0.2 to 20 v/v %, with the range of 0.5 to 10 v/v % being more preferred. An optimum concentration of glacial acetic acid is 2 v/v %. The dilute aqueous solution of acetic acid in which the shaped chitin body is being dipped is held generally at between 10° and 30° C., and preferably at about 25° C. The bath ratio is such that at least 100 parts by weight of the dilute aqueous solution of acetic acid is used for 1 part by weight of the shaped chitin body.

Under the conditions specified above, the shaped chitin body of the present invention will retain its shape without being liquefied for a certain period of time which is preferably at least 1 hour, more preferably at least 3 hours, and optimally at least 12 hours. The "retention of the shape" of the chitin body does not simply mean that it continues to be present in a solid form without being dissolved in the acetic acid solution; it more specifically means that the chitin body retains the shape it assumed before it was dipped in the dilute aqueous solution of acetic acid. For instance, a fibrous chitin will remain fibrous even after it is submerged within the dilute acetic acid solution. The shaped chitin body in accordance with the present invention will not change in shape within the dilute aqueous acetic acid solution, but will swell to gain in volume. The amount of volume increase will vary with the specific form of the chitin body, but it must be at least about 10 times as great as the volume of the chitin in the dry state before it is dipped in the dilute acetic acid solution. If the shaped chitin body in accordance with the present invention is in a fibrous form, it will swell in a 2 v/v % aqueous solution of acetic acid at 25° C. so that its cross-sectional area increases by at least about 10 times, preferably at least 15 times, more preferably 20 to 100 times, the initial value.

The percentage increase in the volume and cross-sectional area of the shaped chitin body can readily be determined by measuring the size of the chitin body before and after dipping in the dilute aqueous acetic acid solution.

If, on the other hand, spherical particles of chitin yet to be alkali-treated are dipped in a 2 v/v % aqueous solution of acetic acid at 25° C., the volumes of individual particles will increase by a factor of about 8. If a fibrous chitin is dipped in the same concentration of acetic acid without being subjected to alkali treatment, the volume and cross-sectional area of the fiber will increase by factors of about 1.5 and 1.8, respectively.

The shaped chitin body of the present invention swells by different degrees in the dilute aqueous solution of acetic acid depending upon the conditions of alkali treatment, and therefore, said chitin body can be provided with varying swell ratios that suit specific uses of such body.

The shaped chitin body of the present invention has both the sturdiness of chitin and the versatile capabilities of chitosan, while exhibiting a strong acid resistance that is not possessed by chitosan. When dipped in a dilute aqueous solution of acetic acid, the chitin body in accordance with the present invention will swell and its volume increases by a factor of at least 10 while retaining its shape. This property will offer a great advantage in practical applications where the shaped chitin body is to be used as an adsorbent, since its effective volume and surface area can be readily increased by a very simple method before the actual use of such body.

Having the properties described above, the shaped chitin body of the present invention has many useful applications, such as metal adsorbents, medical adsorbents, adsorption filters, ion exchangers, enzyme immobilizing carriers, carriers for affinity chromatography, and microcarriers for cell culture.

If the shaped chitin body in accordance with the present invention is in the fibrous form, useful wound dressings can be prepared by processing such body into a nonwoven fabric or fibrous sheet.

The terminology "nonwoven fabric" here means sheets formed of cut or continuous lengths of the chitin fibers. Nonwoven fabrics may be prepared from the alkali-treated chitin fibers by any of the methods commonly known in the art. For example, the fibers are cut to lengths of 5 to 20 mm which are processed into a nonwoven fabric on a general purpose sheeting machine, e.g., TAPPI standard sheeting machine. Alternatively, the cut fibers may be dispersed in water together with a binder such as polyvinyl alcohol, water is removed from below by passage through a filter medium, and a fiber lamination formed on the filter medium is subsequently pressed and dried to form a nonwoven fabric. The desired nonwoven fabric may also be produced by a continuous sheeting machine operating on the same principle as that of the general purpose machine. The nonwoven fabric for use as a wound dressing in the present invention may vary in thickness depending upon the type and severity of wound, and the commonly employed thickness ranges from 0.05 to 1 mm.

The terminology "fibrous sheet" means sheets of chitin fibers in the form of woven fabrics, knitted fabrics, gauzes, or velours. Such sheets may be formed from continuous chitin filaments or its staple fibers by any of the common fiber processing techniques.

The nonwoven fabric or fibrous sheet prepared in accordance with the present invention may be combined with other materials for use as wound dressings in the form of composite laminations.

Wound dressings made of the shaped chitin body in accordance with the present invention will be of great assistance in healing burns and lesions left after excision of skin grafts. When such dressings are applied to skin defect wounds, any exudate will be effectively adsorbed, minimizing its stagnation on the lesion. The dressings will not be liquefied by body fluids and will keep the lesion wet for an extended period, thereby ensuring the intended regeneration of a new skin. Therefore, the wound dressings made of the shaped chitin body in accordance with the present invention can be used effectively for healing not only superficial second degree burn wounds and lesions left after excision of split thickness grafts but also deep second degree burn wounds and lesions left after excision of thicker grafts, such burns and lesions having so far been considered incurable by conventional wound dressings.

The advantages that the wound dressing made of the shaped chitin body in accordance with the present invention has over those formed of chitosan fibers can be summarized as follows. First, wound dressings made of chitosan fibers dissolve in 2 v/v % aqueous solution of acetic acid at 25° C., whereas the wound dressing in accordance with the present invention swell but not dissolve in that acid solution. Secondly, the dressing in accordance with the present invention can be applied for healing deep wounds such as deep second degree burns and deep lesions left after excision of thick grafts. On the other hand, the dressing made of chitosan fibers cannot be used for healing such deep wounds without becoming liquefied within a few days because of such factors as stagnant exudates.

The following Examples are provided for further illustration of the present invention, and are in no way intended as limiting the present invention.

EXAMPLE 1

A solution of a chitin powder (product of Kyowa Yushi Kogyo K. K.) was prepared by the method described in Japanese Patent Publication (unexamined) No. 134101/1983. More specifically, 2 g of the chitin powder was added to 498 g of ice-cooled dimethylacetamide solution containing 8 w/w % LiCl. Under cooling with ice, the mixture was agitated for about 30 minutes until the chitin swelled. Then, the mixture was heated to about 25° C. and agitated for about 1 hour to obtain a transparent chitin solution. This solution was found to have a viscosity of 450 cps at 30° C. on a Brookfield viscometer. The chitin solution was coagulated by dripping into methanol through a nozzle (0.2 mm diameter) and subsequently washed with water to obtain 270 ml of chitin particles having an average diameter of about 2 mm.

The particulate chitin thus prepared was added to an aqueous solution of NaOH (400 g) to make a total of 1,000 ml. The resulting solution was heat treated at 75° C. for 4 hours. After cooling, cyclic washing with water was conducted, and the washed product was vacuum dried to obtain chitin particles having an average diameter of about 0.5 mm.

A portion (50 mg) of the thus prepared particulate chitin was immersed in 50 ml of a 2 v/v % aqueous solution of acetic acid, and two samples of solution were sealed in containers and left for 24 hours, at 25° C. and 37° C., respectively. For each of the temperatures tested, the chitin particles swelled to a diameter of 1.4 mm, indicating a volume increase by a factor of about 22.

TESTING EXAMPLE 1

In order to check if the chitin particles prepared in Example 1 would have capabilities comparable to those of chitosan, the ability of the particles to adsorb metal ions was compared with a particulate chitin that had not been alkali-treated in accordance with the present invention.

Each of the particulate chitin samples (dry weight: 50 mg) was added to 100 ml of a 100 ppm copper solution, and the two solutions were shaken for 24 hours at room temperature. Thereafter, the copper concentration in each solution was determined by an atomic absorption spectrometer. In the solution containing the control particulate chitin, 95 ppm of Cu ions remained, whereas the solution containing the alkali-treated chitin particles prepared in Example 1 had a Cu content of only 53 ppm.

EXAMPLE 2

Ground chitin powders (100 mesh) were treated with 1 N HCl at 4° C. for 1 hour and held within 3 w/v % aqueous NaOH for 3 hours at between 90° and 100° C. so as to remove any ashes and proteins from the chitin powder. By subsequent cyclic washing with water and drying, 80 g of a purified chitin was obtained. This chitin was dissolved in 920 g of dimethylacetamide containing 8 w/w % LiCl at room temperature, producing a highly viscous transparent solution. This solution was transported under pressure with a gear pump and extruded into a coagulating (methanol) bath through a nozzle (50 holes, 0.07 mm diameter each) so as to obtain a multifilament composed of monofilaments with a diameter of 11 $\mu$m.

A portion (ca. 5 g) of the fiber was submerged in 1,000 ml of a heated (80° C.) 40 w/v % aqueous NaOH solution and left to stand for 3 hours with mild stirring. After cooling, the fiber was transferred into 1,000 ml of deionized water and neutralized by addition of a concentrated HCl solution. Following washing with water and vacuum drying, chitin fibers having a monofilament diameter of 11.6 $\mu$m were obtained.

A portion (10 mg) of the chitin fibers was submerged in 50 ml of 2 v/v % aqueous solution of acetic acid and the solution was sealed into a container and left for 2 days at both 25° C. and 37° C. Using a hole glass plate, the fibers floating on the aqueous acetic acid solution were examined microscopically. For each of the temperatures tested, the chitin fibers swelled to a monofilament diameter of 92 $\mu$m, and the cross-sectional areas and volumes of individual filaments were increased by respective factors of about 63 and 500.

COMPARATIVE EXAMPLE 1

The following experiments were conducted in order to compare the alkali-treated chitin fibers as prepared in Example 2 and chitosan fibers with respect to strength and acid resistance.

A chitosan powder (product of Shin-Nihon Kogaku Kogyo Co., Ltd.) was ground to particles of 100 mesh. Fifty grams of these particles was suspended in 900 g of water. To the stirred suspension, 50 g of glacial acetic acid was added to prepare a high viscosity chitosan solution. The resulting solution was transported under pressure with a gear pump and extruded into 20 w/v % NaOH containing methanol through a nozzle (30 holes, 0.07 mm diameter each) so as to obtain a multifilament composed of monofilaments with a diameter of 12 $\mu$m. The fiber was subjected to cyclic washing with methanol and subsequently dried to produce chitosan fibers.

The strength of the so prepared chitosan fibers and that of the alkali-treated chitin fibers prepared in Example 2 were measured with a tension tester (Model UTM-II of Toyo Baldwin Co., Ltd.). The results were 3.2 g/d for the chitin fibers prepared in Example 2 and 1.5 g/d for the chitosan fibers.

The chitosan fibers dissolved in a 2 v/v % aqueous solution of acetic acid.

TESTING EXAMPLE 2

The following experiments were conducted to check if the alkali-treated chitin fibers prepared in Example 2 would adsorb chemical mutagens in tap water.

The activated carbon and dechlorinating agent in a commercial compact water purifier were replaced by about 5 g of the chitin fibers prepared in Example 2. The so modified purifier was attached to the faucet of a tap water-supply pipe and put to normal use for 30 days. The chemical substances adsorbed on the chitin fibers were extracted with methanol and, after removing methanol by evaporation, the extract was dissolved in dimethyl sulfoxide to prepare test samples for checking its mutagenicity. The extract was negative in a DNA repair test using *E. coli* WP-2 and WP-100 (*Mutation Research,* Vol. 48, pp. 195-204(1977)), and positive in an Ames test with *Salmonella* TA-100 in the absence of metabolic activation (*Mutation Research,* Vol. 31, pp. 347-364 (1975)). These data indicate that chemical mutagens in the tap water could be effectively adsorbed on the alkali-treated chitin fibers prepared in Example 2.

EXAMPLE 3

The purified chitin obtained in Example 2 was dissolved in 8 w/w % LiCl containing dimethylacetamide at room temperature so as to provide a chitin concentration of 7 wt %. The resulting high viscosity transparent solution was filtered through a 1,480 mesh stainless steel net under pressure and placed under vacuum to remove bubbles while stirring. The thus treated solution was put into a tank from which it was transported under pressure with a gear pump and discharged into isopropyl alcohol at 60° C. through a nozzle (20 holes, 0.07 mm diameter each) while the coagulated filaments were taken up by a winder through rolls rotating at 7 m/min.

The wound filaments were thoroughly washed with water to remove any residual coagulating agent and solvent. After drying, the filaments were cut to lengths of about 8 mm. The resulting fibers were treated in a 10 N NaOH solution at 100° C. for 3 hours. After further thorough washing and drying, one of the filaments of the fiber was submerged in a 2 v/v % aqueous acetic acid solution for 24 hours at 25° C. The filament swelled and its cross-sectional area and volume increased by respective factors of 39 and 244.

A portion of the dry chitin fibers (0.5 g) and a polyvinyl alcohol powder (0.05 g) were dispersed in 2,000 ml of water, and the dispersion was processed on a No. 177 TAPPI standard sheeting machine (product of Toyo Seiki Seisakusho, Ltd.) to prepare a fiber lamination, which was compressed and dried to make a square sheet (100×100 mm) having a thickness of 0.15 mm. This sheet was sterilized and used as a wound dressing in the following manner.

Two samples of the sheet were attached to a deep second degree burn on the thigh of a 38 year old woman who had spilled boiling water on it. The applied sheets were fastened and protected by a cotton gauze. After 1 week, external observation revealed the following: the surfaces of the sheets retained the initial state and were kept wet without showing any damage. Exudates from the inside of the body were adequately adsorbed on the sheet surfaces and part of the exudates nearly reached the gauze surface. The lesion was also kept wet because of minimum stagnation of exudates in the lesion. Two weeks later, the sheets could be readily peeled from the lesion and a normal regenerating skin had formed there, indicating the complete healing of the burn and hence, the effectiveness of the sheets prepared in this Example as a wound dressing.

EXAMPLE 4

The purified chitin prepared in Example 2 was dissolved in 8 w/w % LiCl containing N-methylpyrrolidone at room temperature so as to provide a chitin concentration of 6 wt %. The resulting high viscosity transparent solution was filtered through a 1,480 mesh stainless steel net under pressure and placed under vacuum to remove bubbles while stirring. The thus treated solution was put into a tank, from which it was transported under pressure with a gear pump and discharged into a coagulating (methanol) bath at 40° C. through a nozzle (40 holes, 0.08 mm diameter each) while the coagulating filaments were taken up by a winder through rolls rotating at 10 m/min. The wound filaments were dried to produce 40 continuous chitin filaments with a total fineness of 60 denier.

Five of such continuous chitin filaments were twisted together and processed by a gauze weaving machine to make a gauze fabric.

This gauze fabric was treated in 10 N NaOH solution at 120° C. for 1 hour and neutralized with dilute HCl. After thorough washing and drying procedures, part of the alkali-treated gauze was dipped in a 2 v/v % aqueous acetic acid solution for 24 hours at 25° C. One of the filaments composing the gauze which had a fineness of about 1.5 denier was found to have a cross-sectional area and volume which were respectively 64 and 512 times their initial values. After sterilization, the alkali-treated gauze was used as a wound dressing for a lesion left on the back of a 43 year old man after excising a relatively thick skin graft. The top of the gauze was covered with a protective cotton gauze. Five days later, much exudate was observed on the surfaces of both the chitin gauze and the overlying cotton gauze, whereas minimum exudate occurred in the lesion, and this was accompanied by the intended formation of granulation. After 13 days, a new skin surface was formed, indicating the rapidity of the healing of the lesion with the aid of the wound dressing prepared in this Example

COMPARATIVE EXAMPLE 2

The chitosan fibers prepared in Comparative Example 1 were cut to lengths of about 8 mm. The resulting dry chitosan fibers (0.5 g) and a polyvinyl alcohol powder (0.05 g) were dispersed in 2,000 ml of water, and the dispersion was processed on a No. 177 TAPPI standard sheeting machine to prepare a square sheet (100×100 mm). This sheet was sterilized and used as a wound dressing in the following manner.

Two samples of the sheet were attached to a deep second degree burn on the back of the neck of a 43 year old man. The sheets were covered and protected by a cotton gauze. After 2 days, the sheets were liquefied and became pulpy because of the exudate from the body, and were no longer effective as the wound dressing.

While the invention has been described in detail and with reference to specific embodiments thereof, it will be apparent to one skilled in the art that various changes and modifications can be made therein without departing from the spirit and scope thereof.

What is claimed is:

1. A shaped chitin body prepared by treating a shaped body of chitin with an alkali solution, such that within an aqueous solution of acetic acid containing 0.1 to 50 percent on a volume/volume basis acetic acid, the volume of said shaped chitin body will increase by a factor of at least about 10 while substantially retaining its shape.

2. A chitin fiber prepared by treating a fiber of chitin with an alkali solution, such that within a 2 percent aqueous solution of acetic acid on a volume/volume basis at 25° C., the cross-sectional area of said chitin fiber will icrease by a factor of at least about 10 while retaining its shape.

3. A wound dressing in the form of a nonwoven fabric or a fibrous sheet that is made using chitin fiber prepared by treating a fiber of chitin with an alkali, and which has a property such that within a 2 percent aqueous solution of acetic acid on a volume/volume basis at 25° C., the cross-sectional area of said chitin fiber will increase by a factor of at least about 10 while retaining its shape.

4. A shaped chitin body as in claim 1, wherein the alkali solutoin is an aqueous solutin of sodium hydroxide having a concentration of at least 0.1 grams sodium hydroxide/100 cc alkali solution.

5. A shaped chitin body as in claim 1, wherein the temperature of the treatment with the alkali solution is at least 10° C.

6. A shaped chitin body as in claim 1, wherein the duration of the treatment with the alkali solution is in the range of from 1 minute to 24 hours.

7. A shaped chitin body as in claim 1, wherein at least 25 parts by weight of the alkali solution is used for treating 1 part by weight of the shaped body of chitin.

8. A chitin fiber as in claim 2, wherein the alkali solution is an aqueous solution of sodium hydroxide having a concentration of at least 0.1 grams sodium hydroxide/100 cc alkali solution.

9. A chitin fiber as in claim 2, wherein the temperature of the treatment with the alkali solution is at least 10° C.

10. A chitin fiber as in claim 2, wherein the duration of the treatment with the alkali solution is in the range of from 1 minute to 24 hours.

11. A chitin fiber as in claim 2, wherein the cross-sectional area increases by at least 15 times the initial value.

12. A chitin fiber as in claim 2, wherein the cross-sectional area increases by 20 to 100 times the initial value.

13. A wound dressing as in claim 3, wherein the alkali solution is an aqueous solution of sodium hydroxide having a concentration of at least 0.1 grams sodium hydroxide/100 cc alkali solution.

14. A wound dressing as in claim 3, wherein the temperature of the treatment with the alkali solution is at least 10° C.

15. A wound dressing as in claim 3, wherein the duration of the treatment with the alkali solution is in the range of from 1 minute to 24 hours.

16. A wound dressing as in claim 3, wherein the cross-sectional area increases by at least 15 times the initial value.

17. A wound dressing as in claim 3, wherein the cross-sectional area increases by 20 to 100 times the initial value.

* * * * *